United States Patent

Aren et al.

[11] 4,113,948
[45] Sep. 12, 1978

[54] 1-AMINO-1-PHTHALIDYL ALKANES AND A METHOD FOR PRODUCING SAME

[76] Inventors: Avgust Karlovich Aren, ulitsa Siltsiema, 15/5, kv. 72, Riga; Irma Arnoldovna Berzinya, ulitsa Rezeknes, 25, kv. 2, Jurmala Latviiskoi SSR; Ivars Petrovich Lentsbergs, ulitsa Zasulauka, 27, kv. 1, Riga, all of U.S.S.R.

[21] Appl. No.: 679,869

[22] Filed: Apr. 23, 1976

Related U.S. Application Data

[63] Continuation of Ser. No. 443,037, Feb. 15, 1974, abandoned.

[51] Int. Cl.² ............................................. C07D 295/00
[52] U.S. Cl. .............................. 544/152; 260/343.3 R; 260/290 H; 260/293.58; 260/239 R; 260/326.8; 544/376
[58] Field of Search ............ 260/343.3, 290 H, 289 R, 260/326.29, 293.58, 239 R, 250 B, 268 PH, 268 H, 326.8

[56]  References Cited
FOREIGN PATENT DOCUMENTS 2,404,633  8/1975  Fed. Rep. of Germany ........ 260/343.3

*Primary Examiner*—Paul J. Killos
*Attorney, Agent, or Firm*—Haseltine, Lake & Waters

[57]  ABSTRACT

The invention comprises 1-amino-1-phthalidyl alkanes of the formula:

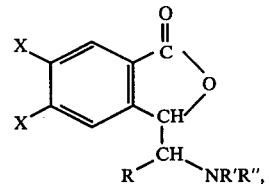

where
X = H, or $CH_3O$;
R = $CH_3$, $C_6H_5$, p—$CH_3OC_6H_4$, or p—$ClC_6H_4$;
R' = H, or $C_2H_5$;
R'' = H, $CH_3$, $C_2H_5$, $C_6H_5CH_2$, $C_6H_5$, or p—$CH_3OC_6H_4$;
R' and R'', when taken together form the radical —$(CH_2)_4$—, —$(CH_2)_5$—, —$(CH_2)_2$—O—$(CH_2)_2$—, —$(CH_2)_2$—N($C_6H_5$)—$(CH_2)_2$—, —$(CH_2)_2$—N(p—$CH_3OC_6H_4$)—$(CH_2)_2$—, or —$(CH_2)_2$—N(—o-$CH_3OC_6H_4$)—$(CH_2)_2$—, and a method for producing same which comprises dissolving α-aminoylidenephthalide of the general formula:

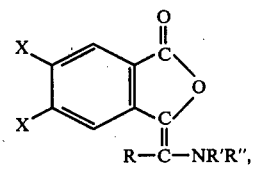

where X, R, R' and R'' are the same as those given above, in dioxane or acetic acid, adding sodium boron hydride or pyridine borane to the solution, maintaining the solution at room temperature till the exocyclic double bond reduction is over, and recovering the end product.

15 Claims, No Drawings

1-AMINO-1-PHTHALIDYL ALKANES AND A METHOD FOR PRODUCING SAME

This is a continuation of application Ser. No. 443,037, filed Feb. 15, 1974 now abandoned.

The present invention relates to aminophthalidyl alkanes and to a method for producing same.

The organic compounds with molecules comprising both an amino group and a γ-lactonic group

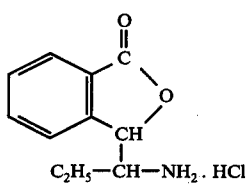
(I)

merit attention as a class of pharmacologically active substances.

It is known that the chloride of 1-amino-1-phthalidyl propane of formula (I) is a potent analgesic.

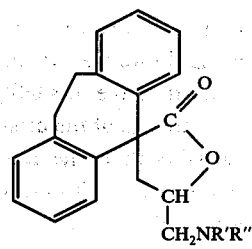
(II)

where R'R" = H, alkyl.

The aminolactones of formula (II) have a pronounced antidepressant effect on mammals.

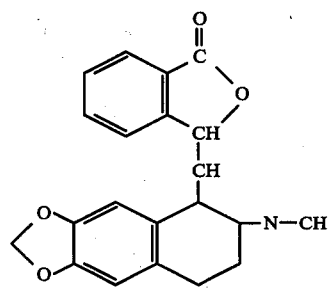
(III)

The aminolactone of formula (III) is an effective antagonist of γ-amino butyric acid (GABA) which blocks the GABA receptors, causing neutron excitation.

Yet, the derivative of formula (IV)

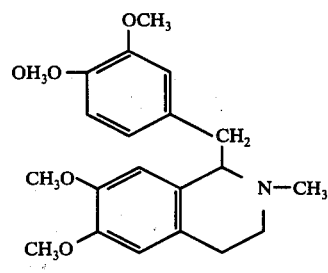
(IV)

which contains no lactonic cycle does not exhibit the aforementioned properties, suggesting that the compound of formula (III) is structurally similar to γ-amino butyric acid. The derivatives of formula (I) are likewise structural analogs of γ-amino butyric acid, so that aminophthalidyl alkanes constitute a good prospect as far as synthesis of pharmacologically active compounds is concerned.

Furthermore, aminophthalidyl alkanes have been described as intermediate products for the synthesis of isoquinolones.

The known routes of aminophthalidyl alkane synthesis are, by and large, limited, to the method of selective reduction of nitrophthalidyl alkanes (Ullyot et al. J. Org. Chem., 10, 429 (1945)):

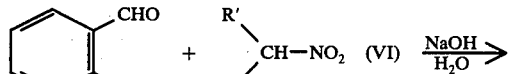
(VI)

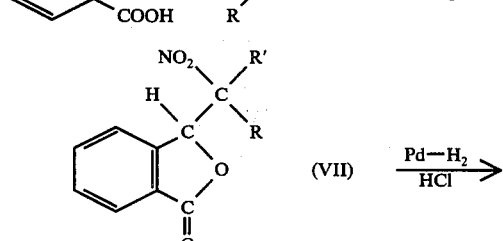
(VII)

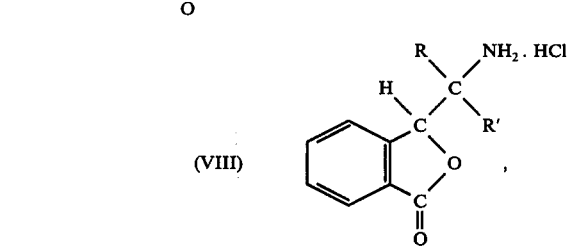
(VIII)

where
R = H, CH₃;
R' = H or n-alkyl (C₁ - C₅).

Reduction of the nitro group is effected on a palladium catalyst, or else electrochemically.

It should be noted that if satisfactory yields of condensation products with the nitro alkanes of formula (VII) are to be secured, the reaction must proceed for several days.

Another, more wide-spread method for synthesizing aminophthalidyl alkanes may be represented by the following flowchart:

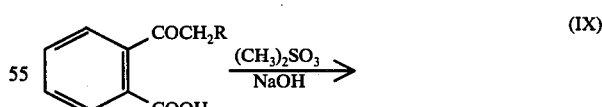
(IX)

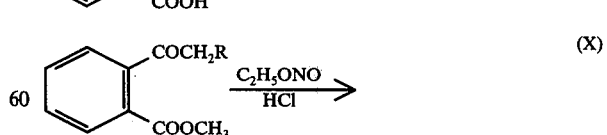
(X)

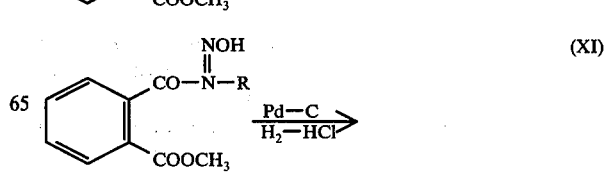
(XI)

-continued

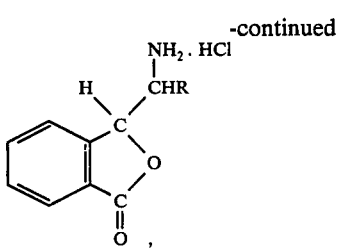

(XII)

where R = $CH_3$, $C_2H_5$.

As can be inferred from the foregoing flowchart, the reaction products are exclusively aliphatic derivatives of aminophthalidyl alkanes (in the compounds of formulas (VIII) and (XII) R and R' are aliphatic radicals).

The other known routes of aminophthalidyl alkane synthesis, such as reduction of 3-cyanolikonin and condensation of catharnin (XIII) with phthalide, are of commercial significance:

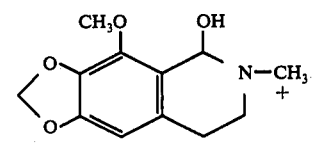

(XIII)

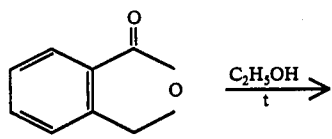

(XIV)

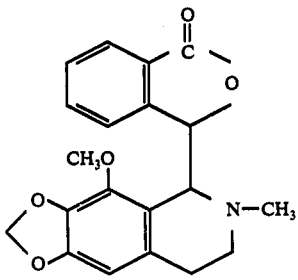

Furthermore, the chemical literature contains nothing in the way of a general method for synthesizing N-substituted aminophthalidyl alkanes, though it is known to synthesize (not commercially) the aforementioned derivative (XIV) and to produce 1-methylamino-1-meconylmethane by N-methylation of primary amino derivative.

As can be seen from the foregoing, the prior art methods for synthesizing aminophthalidyl alkanes involve multiple-step processes and require catalysts of a definite level of activity. No general method exists for synthesizing N-mono, N,N-disubstituted or aryl derivatives of aminophthalidyl alkanes.

It is an object of the present invention to produce aminophthalidyl alkanes of varied complex structure, including those which comprise one or two substituents at the nitrogen atom.

It is another object of the present invention to provide a method for producing the aforementioned compounds with a sufficiently high yield.

Other objects and advantages of the present invention will become apparent from the following detailed description of the invention.

The foregoing objects are attained by producing 1-amino-1-phthalidyl alkanes of the formula:

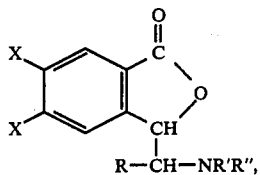

XV where
X = H, $CH_3O$;
R is a radical: $CH_3$, $C_6H_5$, p—$CH_3OC_6H_4$, p—$ClC_6H_4$;
R' is a radical: H, $C_2H_5$;
R" is a radical: H, $CH_3$, $C_2H_5$, $C_6H_5CH_2$, $C_6H_5$, p—$CH_3OC_6H_4$;
R'R" is radical: —$(CH_2)_4$—, —$(CH_2)_5$—, —$(CH_2)_2$—O—$(CH_2)_2$—, —$(CH_2)_2$—N($C_6H_5$)—$(CH_2)_2$—, —$(CH_2)_2$—N—(p—$CH_3O$—$C_6H_4$)—$(CH_2)_2$—, —$(CH_2)_2$—N(O—$CH_3OC_6H_4$—)—$(CH_2)_2$—.

The following structural formulas of individual aminophthalidyl alkanes illustrate the feasibility of obtaining a wide range of compounds of the class in question comprising various substituents in the amino group at the carbon atom which is linked with the amino group in the phthalide ring as well.

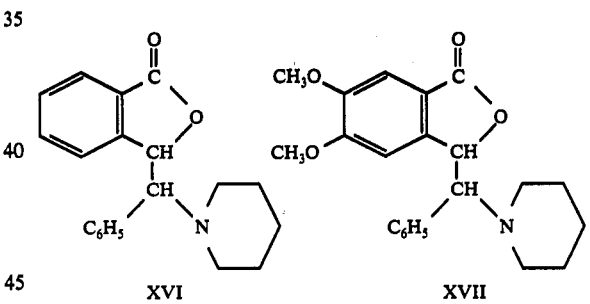

XVI        XVII

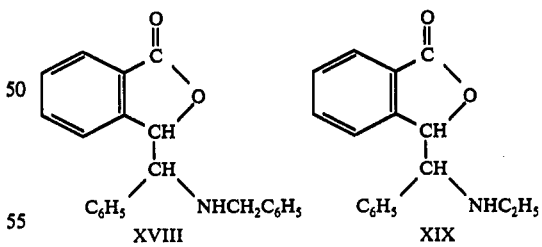

XVIII        XIX

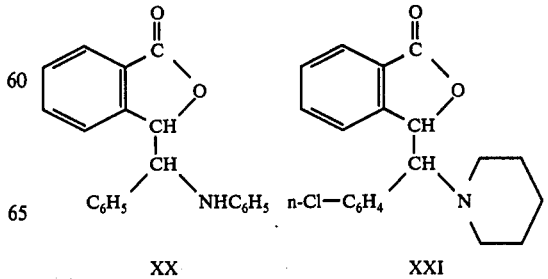

XX        XXI

-continued

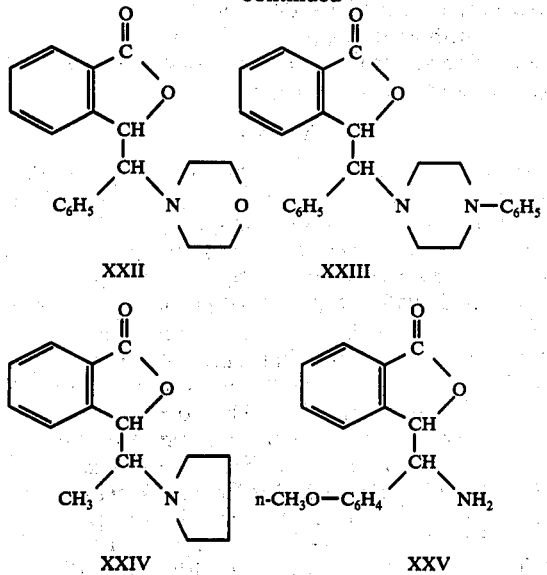

XXII   XXIII   XXIV   XXV

The compounds of formulas XVI to XXV represent various derivatives of 1-amino-1-phthalidyl alkanes which can be produced by the method of the present invention; they testify to the wide scope and universal nature of the proposed method as applied for the production of compounds of this class.

1-amino-1-phthalidyl alkanes are white or yellowish crystalline substances readily soluble in common organic solvents, such as alcohols, benzene, chloroform, acetone, dioxane, etc., and almost insoluble in water.

The structure of synthetic 1-amino-1-phthalidyl alkanes has been corroborated by physico-chemical (IR and UV spectra) and chemical findings.

The IR spectra of all 1-amino-1-phthalidyl alkanes are characterized by an intensive absorption maximum in the 1,771 to 1,757 cm$^{-1}$ range due to the valence vibrations $\nu C = 0$ in $\gamma$-lactone.

1-amino-1-phthalidyl alkanes react with acids to form salts. The chlorides of 1-amino-1-phthalidyl alkanes are white crystalline substances. The IR spectra of aminophthalidyl alkane chlorides show the valence vibration band for lactone carbonyl $\nu C = 0$ at 1,780 cm$^{-1}$.

There is a wide absorption maximum due to the valence vibrations of the ammonium ion $\nu$ H$^+$—H in the 3,000 to 2,200 cm$^{-1}$ range for these salts.

N-unsubstituted and N-monosubstituted aminophthalidyl alkanes easily form N-nitroso and N-acyl derivatives.

In accordance with the invention, the method for producing said 1-amino-1-phthalidyl alkanes comprises dissolving α-aminoylidenephthalide of the general formula:

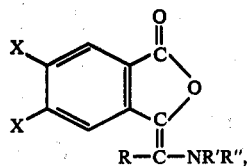

where
X = H, CH$_3$O;
R = CH$_3$, C$_6$H$_5$, p—CH$_3$OC$_6$H$_4$, p—Cl—C$_6$H$_4$;
R' = H, C$_2$H$_5$;
R" = H, CH$_3$, C$_2$H$_5$, C$_6$H$_5$CH$_2$, C$_6$H$_5$, p—CH$_3$OC$_6$H$_4$;
R'R" = —(CH$_2$)$_4$—, —(CH$_2$)$_5$—, —(CH$_2$)$_2$—O—(CH$_2$)$_2$—, —(CH$_2$)$_2$—N(C$_6$H$_5$)—(CH$_2$)$_2$—, —(CH$_2$)$_2$—N(p—CH$_3$OC$_6$H$_4$)— —(CH$_2$)$_2$—(CH$_2$)$_2$—N(ortho—CH$_3$OC$_6$H$_4$)—(CH$_2$)$_2$—, in dioxane or acetic acid, adding sodium boron hydride or pyridine borane, to the solution, maintaining the solution at room temperature until the exocyclic double bond has been reduced, and recovering the end product.

Should sodium boron hydride be employed as the reducing agent, it is recommended to prepare in advance an enamic salt of α-aminoylidenephthalide, for which purpose a solution of α-aminoylidenenphthalide in dioxane is saturated with dry hydrogen chloride, and then sodium boron hydride is added to the solution at the rate of 5 moles per 1 mole of the parent α-aminoylidenephthalide. The reaction mixture is maintained at room temperature till the double bond reduction is over.

Should pyridine borane be employed as the reducing agent in accordance with the invention, α-aminoylidenephthalide is dissolved in acetic acid, and pyridine borane is added to the solution at the rate of 3 moles per 1 mole of the starting α-aminoylidenephthalide.

The reaction is over when the solution loses its greenish-yellow color.

Before recovering the end product, the excess of sodium boron hydride or pyridine borane is decomposed with sulfuric acid, the solution is diluted with water and neutralized with sodium hydroxide solution.

If the end product forms well defined crystals, it is recovered by filtration.

If the end product is contaminated or if it has not crystallized, the end product may be recovered in the form of a chloride.

To this end, sulfuric acid is added by drops to the 24 to 48 hour old reaction mixture until gas liberation has stopped altogether, indicating that the decomposition of the non-reacted sodium boron hydride or pyridine borane is over. Then the reaction mixture is diluted with water and neutralized with alkali hydroxide. If the dioxane solution of α-aminoylidenephthalide requires a great quantity of dioxane, the latter is preferably concentrated prior to being diluted with water. Further, the neutral solution is extracted with ether, the ether extract is dried over magnesium sulfate, filtered off, and the filtrate is saturated with dry hydrogen chloride. In the course of extraction, 1-amino-1-phthalidyl alkane salt precipitates out and is recovered by filtration.

The invention will be better understood from the following description of a preferred embodiment thereof.

6.14 g (0.02 mole) of α-morpholinobenzylidenephthalide (R = C$_6$H$_5$; R'R" = —(CH$_2$)$_2$—O—(CH$_2$)$_2$—; X = H), is dissolved in 60 ml of glacial acetic acid, and 5.58 g (0.06 mole) of pyridine borane is added. In two hours' time the intensely greenish-yellow solution is completely decolorized (decolorization may be used as a criterion of reaction termination). The excess of pyridine borane is decomposed with strong suffuric acid. The solution is diluted with 300 ml of water and neutralized with potassium hydroxide solution.

The product white crystalline substance is filtered off to yield 6.0 g (98%) of 1-morpholino-1-phthalidyl-1- phenylmethane. Crystallization from ethanol gives 5.45 g (88%) of a product with a melting point of 168° to 169° C.

Ultimate analysis and IR spectral data for 1-morpholino-1-phthalidyl-1-phenylmethane are given in the Table.

Other objects and advantages of the present invention will become apparent from the following description of some exemplary embodiments thereof.

EXAMPLE 1

1.52 g (0.005 mole) of α-piperidinobenzylidenephthalide (R = $C_6H_5$; R'R" = —$(CH_2)_5$—; X = H) is dissolved in 10 ml of glacial acetic acid, and 1.40 g (0.015 mole) of pyridine borane is added. The solution is decolorized within 3 minutes. The excess of pyridine borane is decomposed with concentrated sulfuric acid. The solution is diluted with water, neutralized with potassium hydroxide solution and extracted with ether. The ether extract is washed with water, dried over anhydrous magnesium sulfate and saturated with dry hydrogen chloride. The precipitate is filtered off to yield 1.42 g (83%) of the chloride of 1-piperidine-1-phthalidyl-1-phenylmethane in the form of white crystals (the chlorides of aminophthalidyl alkanes earmarked for use in subsequent steps of synthesis need not be recrystallized). After crystallization from ethanol and absolute ether, 1.22 g (71%) of a product with a melting point of 249° C. is obtained. The ultimate analysis and IR spectral data for the product are given in the Table.

EXAMPLE 2

3.65 g (0.01 mole) of α-piperidine-α-phenyl-5,6-dimethoxymethylenephthalide (R = $C_6H_5$; R' and R" = —$(CH_2)_5$—; X = $CH_3O$) is dissolved in 100 g of glacial acetic acid, and 2.79 g (0.03 mole) of pyridine borane is added. In 90 minutes the intensely green-yellow solution is completely decolorized. The excess pyridine borane is decomposed by adding, by drops, concentrated sulfuric acid until gas liberation has stopped completely. The solution is diluted with 500 ml of water and neutralized with potassium hydroxide solution.

The product substance is in the form of white crystals. Filtration and drying give 3.44 g (94%) of 1-piperidino-1—(5,6-dimethoxyphthalidyl)-1-phenylmethane. Crystallization from a mixture of ethanol and dioxane (1:1) yields 3.1 g (85% of the theoretical) of a product with a melting point of 213° to 214° C.

The ultimate analysis and IR spectral data for the product are given in the Table.

EXAMPLE 3

4.90 g (0.015 mole) of α-benzylamino-benzylidenephthalide (R = $C_6H_5$; R' = H; R" =$C_6H_5CH_2$; X = H) is dissolved in 40 ml of absolute dioxane, and dry hydrogen chloride is bubbled through the solution. 10 to 15 minutes of this procedure causes the dioxane solution to grow turbid, with fine crystals precipitating out. 2.84 g (0.075 mole) of sodium boron hydride is added to this suspension. The solution is maintained at room temperature for 2 days, after which the excess of the reducing agent is decomposed with weak hydrochloric acid, the acid solution is diluted with a triple amount of water, neutralized with alkali hydroxide and extracted with ether. The ether extract is dried over magnesium sulfate, filtered off and saturated with dry hydrogen chloride. The resultant white precipitate is filtered off to yield 3.60 g (65%) of 1-benzylamino-1-phthalidyl-1-phenylmethane chloride. Crystallization from absolute methanol with absolute ether added yields 3.10 g (56% of the theoretical) of a product with a melting point of 255° to 257° C.

The ultimate analysis and IR spectral data for the aminophthalidyl alkanes synthesized are given in the Table.

EXAMPLES 4 – 8

Under conditions duplicating those of Example 1, compounds are obtained which are given in the Table under Nos 4 – 8

EXAMPLE 9 – 13

Under conditions duplicating those of Example 2, compounds are obtained which are given in the Table under Nos 9 – 13.

EXAMPLES 14 AND 15

Under conditions duplicating those of Example 3, compounds are obtained which are given in the Table under Nos 14 and 15.

METHOD FOR PRODUCING AMINOPHTHALIDYL ALKANES

| No. of example | R | R' | R" | X | Ultimate formula |
|---|---|---|---|---|---|
| 1 | 2 | 3 | 4 | 5 | 6 |
| 1 | $C_6H_5$ | | —$(CH_2)_5$— | H | $C_{20}H_{21}O_2N \cdot HCl$ |
| 2 | $C_6H_5$ | | —$(CH_2)_5$— | $CH_3O$ | $C_{22}H_{25}O_4N$ |
| 3 | $C_6H_5$ | H | $C_6H_5CH_2$ | H | $C_{22}H_{19}O_2N \cdot HCl$ |
| 4 | $C_6H_5$ | H | $C_2H_5$ | H | $C_{17}H_{17}O_2N \cdot HCl$ |
| 5 | $C_6H_5$ | H | $C_6H_5$ | H | $C_{21}H_{17}O_2N \cdot HCl$ |
| 6 | $C_6H_5$ | H | p—$CH_3O$—$C_6H_4$ | H | $C_{22}H_{20}O_3N$—HCl |
| 7 | $C_6H_5$ | $C_2H_5$ | $C_2H_5$ | H | $C_{19}H_{21}O_2N \cdot HCl$ |
| 8 | p—Cl—$C_6H_4$ | | —$(CH_2)_5$— | H | $C_{20}H_{20}O_2NCl \cdot HCl$ |
| 9 | $C_6H_5$ | | —$(CH_2)_2$—O—$(CH_2)_2$— | H | $C_{19}H_{19}O_3N$ |
| 10 | $C_6H_5$ | H | $CH_3$ | H | $C_{16}H_{15}O_2N$ |
| 11 | $C_6H_5$ | | —$(CH_2)_2$—N—$(C_6H_5) \cdot (CH_2)_2$— | H | $C_{25}H_{24}O_2N_2$ |
| 12 | $C_6H_5$ | | —$(CH_2)_2$—N(p-$CH_3O \cdot C_6H_4$)—$(CH_2)_2$— | H | $C_{26}H_{26}O_3N$ |
| 13 | $C_6H_5$ | | —$(CH_2)_2$N—(o-$CH_3O \cdot C_6H_4$)—$(CH_2)_2$— | H | $C_{26}H_{26}O_3N$ |
| 14 | $CH_3$ | | —$(CH_2)_4$— | H | $C_{14}H_{17}O_2N \cdot HCl$ |
| 15 | p—$CH_3OC_6H_4$ | H | H | H | $C_{16}H_{15}O_3N \cdot HCl$ |

| Reaction time, hr | m.p. ° C | Crystallization solvent | Yield, % prior to crystallization | after crystallization |
|---|---|---|---|---|

-continued

METHOD FOR PRODUCING AMINOPHTHALIDYL ALKANES

| | | | | |
|---|---|---|---|---|
| 0.05 | 248–249 | methanol-ether | 83 | 71 |
| 1.5 | 213–214 | ethanol-dioxane | 94 | 85 |
| 48 | 255–257 | methanol-ether | 65 | 56 |
| 2.0 | 280 | " | 79 | 70 |
| 24 | 189–195 | " | 59 | 42 |
| 24 | 229–232 | " | 69 | 58 |
| 1.0 | 229–230 | " | 81 | 77 |
| 1.0 | 246–248 | " | 78 | 67 |
| 2.0 | 168–169 | ethanol | 98 | 88 |
| 1.0 | 104 | " | 84 | 73 |
| 2.0 | 177 | ethylacetate:hexane (1:1) | 78 | 70 |
| 2.0 | 174–175 | " | 81 | 73 |
| 2.0 | 163 | " | 77 | 68 |
| 48 | 214–216 | methanol-ether | 51 | 42 |
| 48 | 235–237 | " | 53 | 40 |

| Estimated, % | | | | Actual, % | | | | IR Spectra, |
|---|---|---|---|---|---|---|---|---|
| C | H | N | Cl | C | H | N | Cl | cm$^{-1}$ |
| 12 | 13 | 14 | 15 | 16 | 17 | 18 | 19 | 20 |
| 69.86 | 6.44 | 4.07 | 10.31 | 69.64 | 6.30 | 3.92 | 10.21 | 1777 |
| 71.91 | 6.86 | 3.81 | — | 71.72 | 6.68 | 3.89 | — | 1760 |
| 72.23 | 5.51 | 3.83 | 9.69 | 72.48 | 5.52 | 3.90 | 9.49 | 1777 |
| 67.21 | 5.97 | 4.63 | 11.67 | 67.44 | 6.06 | 4.82 | 11.80 | 1781 |
| 71.69 | 5.16 | 3.98 | 10.07 | 72.01 | 5.22 | 3.80 | 9.80 | 1782 |
| 69.25 | 3.67 | 5.25 | 9.30 | 69.29 | 5.24 | 3.74 | 9.08 | 1784 |
| 69.01 | 6.64 | 4.24 | 10.71 | 68.87 | 6.72 | 4.29 | 10.60 | 1781 |
| — | — | 3.73 | 18.61 | — | — | 3.70 | 18.74 | 1778 |
| 73.77 | 6.19 | 4.53 | — | 73.56 | 6.20 | 4.67 | — | 1759 |
| 75.87 | 5.97 | 5.53 | — | 75.61 | 5.78 | 5.61 | — | 1757 |
| 78.09 | 6.29 | 7.28 | — | 78.49 | 6.48 | 7.49 | — | 1775 |
| 75.34 | 6.32 | 6.75 | — | 75.04 | 6.38 | 6.91 | — | 1762 |
| " | " | " | — | 75.55 | 6.20 | 6.81 | — | 1760 |
| 62.80 | 6.78 | 5.23 | 13.24 | 62.65 | 6.96 | 5.28 | 13.36 | 1762 |
| — | — | 4.58 | 11.60 | — | — | 4.55 | 11.76 | 1766 |

What is claimed is:

1. A 1-amino-1-phthalidyl alkane of the formula:

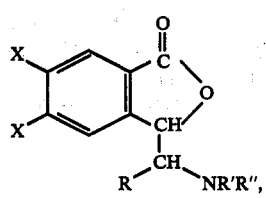

wherein:
X = is selected from the group consisting of H, and CH$_3$O;
R is a radical selected from the group consisting of: CH$_3$, C$_6$H$_5$, p—CH$_3$OC$_6$H$_4$ and p—ClC$_6$H$_4$;
R′ is a radical selected from the group consisting of: H, and C$_2$H$_5$;
R″ is a radical selected from the group consisting of: H, CH$_3$, C$_2$H$_5$, C$_6$H$_5$CH$_2$, C$_6$H$_5$, and p—CH$_3$OC$_6$H$_4$
R′ and R″, when taken together, form a radical selected from the group consisting of: —(CH$_2$)$_4$—, —(CH$_2$)$_5$—; —(CH$_2$)$_2$—O—(CH$_2$)$_2$—; —(CH$_2$)$_2$—N(C$_6$H$_5$)—(CH$_2$)$_2$—; —(CH$_2$)$_2$—N(p—CH$_3$O—C$_6$H$_4$—)—(CH$_2$)$_2$—; and —(CH$_2$)$_2$—N(o—CH$_3$OC$_6$H$_4$—)—(CH$_2$)$_2$—.

2. 1-amino-1-phthalidyl alkane as set forth in claim 1, of the formula:

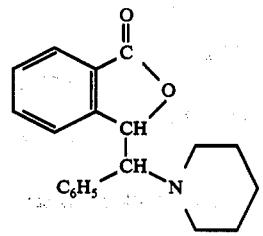

3. 1-amino-1-phthalidyl alkane as set forth in claim 1, of the formula:

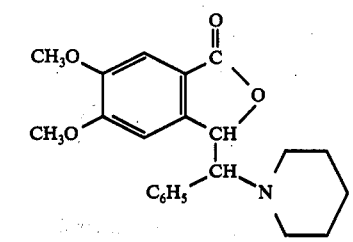

4. 1-amino-1-phthalidyl alkane as set forth in claim 1, of the formula:

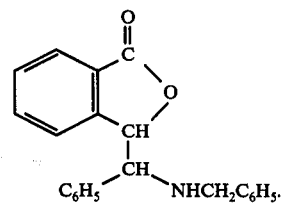

5. 1-amino-1-phthalidyl alkane as set forth in claim 1, of the formula:

6. 1-amino-1-phthalidyl alkane as set forth in claim 1, of the formula:

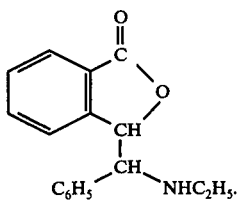

7. 1-amino-1-phthalidyl alkane as set forth in claim 1, of the formula:

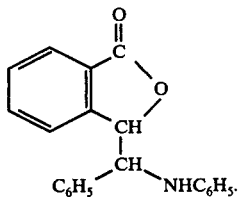

8. 1-amino-1-phthalidyl alkane as set forth in claim 1, of the formula:

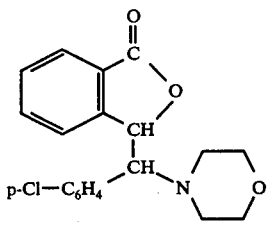

9. 1-amino-1-phthalidyl alkane as set forth in claim 1, of the formula:

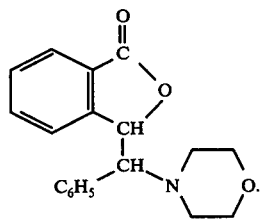

10. 1-amino-1-phthalidyl alkane as set forth in claim 1, of the formula:

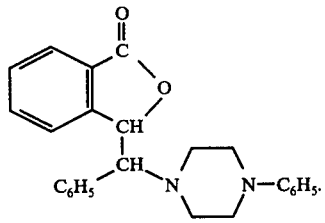

11. 1-amino-1-phthalidyl alkane as set forth in claim 1, of the formula:

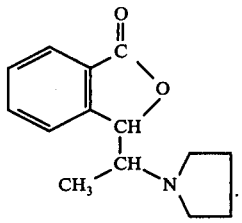

12. A method for producing a 1-amino-1-phthalidyl alkane of the formula:

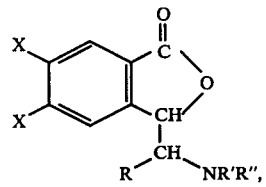

wherein
X — H, or CH$_3$O;
R — CH$_3$, C$_6$H$_5$, p—CH$_3$OC$_6$H$_4$, or p—Cl—C$_6$H$_4$,
R' — H, or C$_2$H$_5$;
R" — H, C$_2$H$_5$, CH$_3$, C$_6$H$_5$CH$_2$, C$_6$H$_5$, or p—CH$_3$OC$_6$H$_4$;
R'R"— —(CH$_2$)$_4$—, —(CH$_2$)$_5$—, —(CH$_2$)$_2$—O—(CH$_2$)$_2$—, —(CH$_2$)$_2$— —N(C$_6$H$_5$)—(CH$_2$)$_2$—; —(CH$_2$)$_2$—N(p—CH$_3$OC$_6$H$_4$)—(CH$_2$)$_2$— or —(CH$_2$)$_2$—N(o—CH$_3$OC$_6$H$_4$)—(CH$_2$)$_2$—;

which comprises dissolving an α-aminoylidenephthalide of the formula:

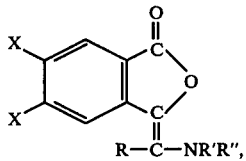

where R, R', R" and X are the same as those given hereabove, in an organic solvent selected from the group consisting of dioxane and acetic acid, adding to the solution a reducing agent selected from the group comprising sodium boron hydride and pyridine borane, maintaining the reaction mixture at room temperature till the end of the reaction of exocyclic double bond reduction, and recovering the end product.

13. A method for producing a 1-amino-1-phthalidyl alkane as set forth in claim 12, which comprises dissolving said α-aminoylidenephthalide in dioxane, saturating said solution with dry hydrogen chloride, adding to said solution sodium boron hydride at the rate of 5 moles per 1 mole of the starting α-aminoylidenephthalide, maintaining the reaction mixture at room temperature till the end of the reaction of exocyclic double bond reduction, and recovering the end product.

14. A method for producing a 1-amino-1-phthalidyl alkane as set forth in claim 12, which comprises dissolving said α-aminoylidenephthalide in acetic acid, adding to said solution pyridine borane at the rate of 3 moles per 1 mole of the starting α-aminoylidenephthalide, maintaining the reaction mixture at room temperature till the end of the reaction of exocyclic double bond reduction, and recovering the end product.

15. A 1-amino-1-phthalidyl alkane of the formula:

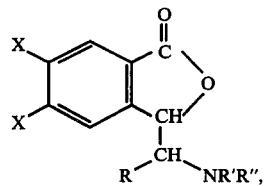

wherein:
X = selected from the group consisting of H, and $CH_3O$;
R is a radical selected from the group consisting of $C_6H_5$, p—$CH_3OC_6H_4$ and p—$ClC_6H_4$;
R' and R", when taken together, form a radical selected from the group consisting of —$(CH_2)_4$—, —$(CH_2)_5$—; —$(CH_2)_2$—O—$(CH_2)_2$—; —$(CH_2)_2$—N($C_6H_5$)—$(CH_2)_2$—; —$(CH_2)_2$—N(p—$CH_3O$—$C_6H_4$—)—$(CH_2)_2$—; and —$(CH_2)_2$—N(o—$CH_3OC_6H_4$—)—$(CH_2)_2$—.

* * * * *